US010100207B2

(12) United States Patent
Stache et al.

(10) Patent No.: US 10,100,207 B2
(45) Date of Patent: Oct. 16, 2018

(54) ADDUCTS OF ISOCYANATOALKYLTRIMETHOXY-SILANES WITH FLAME RETARDANTS REACTIVE THEREWITH

(71) Applicant: Evonik Degussa GmbH, Essen (DE)

(72) Inventors: Wiebke Stache, Herten (DE); Andre Raukamp, Marl (DE); Markus Hallack, Schermbeck (DE); Annegret Lilienthal, Dorsten (DE); Sina Ballauf, Duisburg (DE)

(73) Assignee: Evonik Degussa GmbH, Essen (DE)

( * ) Notice: Subject to any disclaimer, the term of this patent is extended or adjusted under 35 U.S.C. 154(b) by 302 days.

(21) Appl. No.: 15/094,543

(22) Filed: Apr. 8, 2016

(65) Prior Publication Data

US 2016/0297974 A1 Oct. 13, 2016

(30) Foreign Application Priority Data

Apr. 9, 2015 (EP) .................................... 15162900

(51) Int. Cl.
| C09D 5/18 | (2006.01) |
| C09K 21/14 | (2006.01) |
| C09D 185/02 | (2006.01) |
| C07F 7/18 | (2006.01) |
| C07F 9/40 | (2006.01) |

(52) U.S. Cl.
CPC .............. *C09D 5/18* (2013.01); *C07F 7/1804* (2013.01); *C09D 185/02* (2013.01); *C09K 21/14* (2013.01); *C07F 9/4071* (2013.01)

(58) Field of Classification Search
None
See application file for complete search history.

(56) References Cited

U.S. PATENT DOCUMENTS

| 2,843,615 A * | 7/1958 | Linville | C07F 9/4012 376/900 |
| 2,995,594 A * | 8/1961 | Fekete | C07F 9/02 528/24 |
| 2,996,530 A * | 8/1961 | Fekete | C07F 9/02 508/205 |
| 3,122,581 A * | 2/1964 | Pike | C07F 9/02 252/573 |
| 4,093,641 A * | 6/1978 | Plueddemann | C08G 79/04 556/405 |
| 4,333,843 A * | 6/1982 | Wing | C09K 5/20 252/74 |
| 4,367,154 A * | 1/1983 | Jernigan | C09K 5/20 252/78.3 |
| 4,370,255 A * | 1/1983 | Plueddemann | C23F 11/08 252/389.22 |
| 4,900,857 A * | 2/1990 | Klett | C07F 9/5004 556/405 |
| 5,456,984 A * | 10/1995 | Bishop | C03C 25/106 428/373 |
| 7,041,709 B2 * | 5/2006 | Klee | A61K 6/0008 522/37 |
| 7,144,935 B2 * | 12/2006 | Seidel | C08K 5/5406 524/130 |
| 7,887,690 B2 | 2/2011 | Hayashi et al. | |
| 8,334,875 B2 | 12/2012 | Matsusaka et al. | |
| 2002/0146382 A1 * | 10/2002 | Mallo | A61K 8/898 424/70.122 |
| 2011/0086234 A1 * | 4/2011 | Stasko | C09D 5/08 428/447 |
| 2013/0066009 A1 * | 3/2013 | Backer | C08G 77/26 524/537 |
| 2013/0244043 A1 | 9/2013 | Lomoelder et al. | |
| 2016/0032045 A1 | 2/2016 | Diehl et al. | |

FOREIGN PATENT DOCUMENTS

| CN | 103304883 A | 9/2013 |
| DE | 10 2012 204 290 A1 | 9/2013 |
| JP | 48-24386 B1 | 7/1973 |
| JP | 51-19047 A | 2/1976 |
| JP | 55-58282 A | 4/1980 |
| JP | 62-500307 A | 2/1987 |
| JP | 2002-226770 A | 8/2002 |
| JP | 2002-532612 A | 10/2002 |
| JP | 2004-533413 A | 11/2004 |
| JP | 2009-513806 A | 4/2009 |
| JP | 2011-213638 A | 10/2011 |
| JP | 2012-521454 A | 9/2012 |
| JP | 2013-92435 A | 5/2013 |
| JP | 2014-218593 A | 11/2014 |
| KR | 10-2012-0060980 A | 6/2012 |
| WO | WO 2014/139858 A1 | 9/2014 |

OTHER PUBLICATIONS

Technical data sheet for Exolit OP 560, 4 pages, 2013. (Year: 2013).*
Extended European Search Report dated Sep. 24, 2015 in Patent Application No. 15162900.3 (with English Translation of categories of cited documents).
Katalin Bocz, et al., "Flax fibre reinforced PLA/TPS biocomposites flame retarded with multifunctional additive system", Polymer Degradation and Stability, vol. 106, XP028854219, Nov. 7, 2013, pp. 63-73.

* cited by examiner

*Primary Examiner* — Robert S Loewe

(74) *Attorney, Agent, or Firm* — Grüneberg and Myers PLLC

(57) ABSTRACT

An adduct of at least one isocyanatoalkyltrimethoxysilane with at least one flame retardant reactive with the isocyanatoalkyltrimethoxysilane is used in compositions and for coating plexiglass.

17 Claims, No Drawings

ADDUCTS OF ISOCYANATOALKYLTRIMETHOXY-SILANES WITH FLAME RETARDANTS REACTIVE THEREWITH

BACKGROUND OF THE INVENTION

Field of the Invention

The present invention relates to an adduct of a isocyanatoalkyltrimethoxysilane with a flame retardant reactive therewith, to methods of preparing said adduct, to compositions comprising said adduct and to the use thereof.

Discussion of the Background

Binders with trialkoxysilane functionality have a great many applications, for example in scratch-resistant coating compounds (WO 2013/189882 A2), hot-melt adhesives (U.S. Pat. No. 8,535,798 B2) and sealing compounds (DE 10 2012 203273 A1) since such binders have a high degree of crosslinking on account of the trialkoxysilane structural elements they comprise.

For many applications, particularly in the public sector, sufficient flame retardancy is desirable not only for the substrates employed in the respective application but also for their surface coatings, adhesive compounds and sealing compounds. Such formulations often have unreactive flame retardants added to them along with individual formulation constituents in order to retard or even completely inhibit combustion. Examples of flame retardants employed include mineral substances, for example aluminum hydroxide or antimony oxide, and (in particular halogen- or phosphorus-containing) organic flame retardants. However, the disadvantage of additive flame retardants is that they can migrate out of the applied surface coatings/adhesive compounds thus resulting in undesired emission and reduction of the flame retardant activity.

Another disadvantage is the fact that typical trialkoxysiloxane-based binders have no flame retardant activity.

Marosi et al. (Polymer Degradation and Stability 106 (2014) 63-73) describe a phosphorus-containing triethoxysilane employed for preparing flame retardant biocomposites. However, the disadvantage here is that the flax fibers wetted with the described triethoxysilane need to be heated to high temperatures for long periods to achieve curing. Marosi et al, even cites temperatures of 130° C. and reaction times of 8 h. Such flame retardant adducts are thus not suitable for processing at low temperatures. Another disadvantage is that coatings cured at low temperatures, in particular clearcoats, which comprise such phosphorus-containing triethoxysilane compounds are very tacky.

SUMMARY OF THE INVENTION

It is an object of the present invention to avoid the disadvantages of the related art. More particularly, it is an object of the present invention to provide a flame retardant alkoxysilane processable at low temperatures which may be used for producing non-tacky coatings.

The present invention relates to an adduct of at least one isocyanatoalkyltrimethoxysilane with at least one flame retardant reactive with the isocyanatoalkyltrimethoxysilane.

In another embodiment, the present invention relates to a method of preparing an adduct as above, said method comprising:

reacting the at least one isocyanatoalkyltrimethoxysilane with the at least one flame retardant reactive with the isocyanatoalkyltrimethoxysilane.

In yet another embodiment, the present invention relates to a composition, comprising:

at least one adduct as above.

The present invention further provides a flame retardant coating, adhesive or sealing compound, comprising:

the at least one adduct as above.

In addition, the present invention provides a plexiglass, coated with an adduct as above.

DETAILED DESCRIPTION OF THE INVENTION

All ranges below include all values and subvalues between to lower and upper limit of the range.

The present invention relates to an adduct of at least one isocyanatoalkyltrimethoxysilane with at least one flame retardant reactive with the isocyanatoalkyltrimethoxysilane. The adduct according to the invention may thus be regarded as a reaction product of one or more isocyanatoalkyltrimethoxysilanes with one or more flame retardants reactive with the isocyanaloalkyltrimethoxysilane. The adduct is preferably the reaction product of one isocyanatoalkyltrimethoxysilane with one flame retardant reactive with this isocyanatoakyltrimethoxysilane.

Isocyanatoalkyltrimethoxysilanes and the synthesis thereof are related art. A particularly good flame retardant activity and/or employability at particularly low temperatures over short reaction times may be achieved with isocyanatoalkyltrimethoxysilanes selected from the group consisting of isocyanatomethyltrimethoxysilane, 2-isocyanatoethyltrimethoxysilane, 3-isocyanato-n-propyltrimethoxysilane and 4-isocyanato-n-butyltrimethoxysilane. Very particularly good results may be achieved with 3-isocyanato-n-propyltrimethoxysilane.

The term flame retardants is to be understood as meaning chemical substances which reduce the flammability of materials. Preferred flame retardants are halogen-free. The term halogen-free flame retardants is to be understood as meaning flame retardants comprising phosphorus, nitrogen, aluminum and/or magnesium. Particularly preferred flame retardants are organophosphorus compounds.

The term "reactive" flame retardants is to be understood as meaning retardants which are reactive with at least one of the respective composition constituents and may therefore be incorporated into the particular coating compound, the adhesive/the sealing compound on account of successful bonding. In the present case the bonding of the flame retardant is achieved via the formation of a chemical bond between the isocyanatoalkyltrimethoxysilane and the reactive flame retardant. The successful incorporation makes it possible to avoid undesired emission and thus a loss of flame retardant activity to the greatest possible extent. EP 1 544 7 A1, EP 1 710 264 B1 and US 2012/0296013 A1 describe organophosphorus flame retardants suitable for incorporation into epoxy resins for example.

Organophosphorus flame retardants suitable for adduct formation with isocyanatoalkyltrimethoxysilane preferably comprise hydroxyl, amino and/or thiol radicals which can react by addition reaction with the free isocyanate groups of the isocyanatoalkyltrimethoxysilane.

Examples of incorporable phosphorus-containing flame retardants include 3-(hydroxyphenylphosphinyl)propanoic acid and derivatives thereof. Preference is given to phosphonates or phosphine oxides having on average 1.5 to 3.0 Zerewitinoff-active hydrogen atoms and a number-average molecular weight $M_n$ of 60 to 10 000 Daltons (determined by mass spectrometry). The term Zerewitinoff-active hydrogen atom-containing compounds is further preferably to be understood as meaning compounds comprising hydroxyl, amino and/or thiol radicals.

Preferred compounds have the structural formula

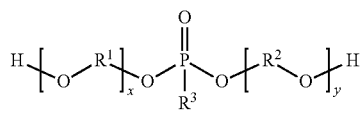

(1)

where $R^1$, $R^2$ branched or unbranched alkylene radical laving 1 to 24 carbon atoms, substituted or unsubstituted arylene radical having 6 to 20 carbon atoms, substituted or unsubstituted aralkylene radical having 6 to 30 carbon atoms, substituted or unsubstituted alkarylene radical having 6 to 30 carbon atoms, wherein $R^1$ and $R^2$ may be identical or different, $R^3$=H, branched or unbranched alkyl radical having 1 to 24 carbon atoms, substituted or unsubstituted aryl radical having 6 to 20 carbon atoms, substituted or unsubstituted aralkyl radical having 6 to 30 carbon atoms, substituted or unsubstituted alkaryl radical having 6 to 30 carbon atoms and x, y=1 to 50.

Likewise preferred compounds have the structural formula

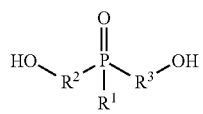

(2)

where $R^1$=H, branched or unbranched alkyl radical having 1 to 24 carbon atoms, substituted or unsubstituted aryl radical having 6 to 20 carbon atoms, substituted or unsubstituted aralkyl radical having 6 to 30 carbon atoms, substituted or unsubstituted alkaryl radical having 6 to 30 carbon atoms, $R^2$, $R^3$=branched or unbranched alkylene radical having 1 to 24 carbon atoms, substituted or unsubstituted arylene radical having 6 to 20 carbon atoms, substituted or unsubstituted aralkylene radical having 6 to 30 carbon atoms, substituted or unsubstituted alkarylene radical having 6 to 30 carbon atoms, wherein the alkyl or aryl radicals may also be substituted with hydroxyl groups, amino groups and/or thiol groups and the radicals $R^2$ and $R^3$ may be identical or different.

It is particularly preferable, because this makes it possible to obtain systems having particularly good light and weathering stability, when the radicals $R^1$, $R^2$ and $R^3$ in formula (1) are branched or unbranched alkyl/alkylene radicals having 1 to 24 carbon atoms, wherein the radicals $R^1$ and $R^2$ may be identical or different.

It is particularly preferable, because this makes it possible to obtain systems having particularly good light and weathering stability, when the radicals $R^1$, $R^2$ and $R^3$ in formula (2) are branched or unbranched alkyl/alkylene radicals having 1 to 24 carbon atoms, wherein the alkyl radicals may also be substituted with hydroxyl groups, amino groups and/or thiol groups and the radicals $R^2$ and $R^3$ may be identical or different.

Further preferred incorporable organophosphorus flame retardants are phosphonic acid esters, in particular dimethyl methylphosphonate, diethyl-N,N-bis(2-hydroxyethyl)aminomethyl phosphonate and dimethylpropane phosphonate.

Commercially available products that are advantageously employable include, for example, the products Exolit OP550 (Clariant, oligomeric organophosphate), Exolit OP 560 (Clariant, corresponds to structural formula (1) where [—OR$^1$—]$_x$=[—R$^1$O—]$_y$=oligo(ethylene glycol) and $R^3$=CH$_3$), Aflammit TL1231 (Thor, corresponds to structural formula (2) where $R^1$=CH$_2$OH and $R^2$=$R^3$=CH$_2$).

It is very particularly preferable when the at least one organophosphorus compound is organophosphate of formula (3)

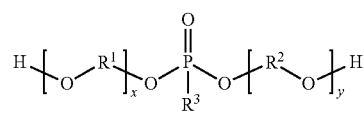

(3)

where
$R^1$=$R^2$=CH$_2$,
$R^3$=CH$_3$
x=0-4 and
y=0-4.

It is further preferable when x or y is at least 2, i.e. the above formula applies with the proviso that x or y 2-4.

Depending on the chosen stoichiometry of the two reaction partners in the adduct formation the adduct from the reaction of at least one, preferably one, isocyanatoalkyltrialkoxysilane with at least one, preferably one, reactive flame retardant may still comprise free hydroxyl or isocyanate groups. However, said adduct is preferably substantially free of hydroxyl or isocyanate groups. It is thus preferably a 1:1 adduct of isocyanatoalkyltrimethoxysilane with flame retardant.

The present invention further provides a method of preparing the adducts according to the invention which comprises reacting at least one, preferably one, isocyanatoalkyltrimethoxysilane with at least one, preferably one flame retardant reactive with the isocyanatoalkyltrimethoxysilane.

The preferred isocyanatoalkyltrimethoxysilanes and flame retardants reactive therewith which are employable in the method according to the invention are the same as those defined previously for the adduct itself.

The reaction of isocyanatoalkyltrimethoxysilane and flame retardant reactive therewith is preferably performed with a ratio of NCO-reactive radicals of the flame retardant(s), in particular of OH, NH$_2$ or SH radicals, to NCO radicals of isocyanatoalkyltrimethoxysilane of 0.8:1 to 1.2:1, preferably 0.9:1 to 1.1:1, with stoichiometric reaction (i.e. in the ratio 1:1) being particularly preferred. It is thus preferable to achieve complete conversion of all NCO-reactive groups of the reactive flame retardant with the NCO groups of the isocyanatoalkyltrimethoxysilane.

In the cited reaction the NCO radicals of the isocyanatoalkyltrialkoxysilane react with the NCO-reactive radicals of the flame retardant. It is preferable when OH, NH$_2$ or SH radicals of the flame retardant are converted into —NH—CO—O—, —NH—CO—NH— or —NH—CO—S— units which link the isocyanatoalkyltrimethoxysilane with the flame retardants.

The reaction may further be performed using typical assistants and added substances, for example solvents and catalysts.

The reaction to afford the adduct according to the invention is preferably performed in the absence of solvent or using aprotic solvents and the reaction may be performed in batchwise or continuous fashion. The reaction may be performed at room temperature, i.e. at temperatures in the range 20-25° C., but preference is given to using higher temperatures in the range 30-150° C., in particular in the range 50-150° C. The reaction is preferably carried out in the absence of water.

To accelerate the reaction, catalysts may advantageously be employed, in particular tertiary and aromatic amines (more particularly triethylamine, pyridine, methylpyridine, benzyldimethylamine, N,N-endoethylenepiperazine, N-methylpiperidine, pentamethyldiethylenetriamine, N,N-dimethylaminocyclohexane, N,N'-dimethylpiperazine). Likewise preferably employable catalysts are metal salts (in particular iron(II) chloride, aluminum tri(ethylacetoacetate), zinc chloride, zinc(II) n-octanoate, zinc(II) 2-ethyl-1-hexanoate, zinc(II) 2-ethylcaproate, zinc(II) stearate, zinc (II) naphthenate, zinc(II) acetylacetonate, tin (II) n-octanoate, tin(II) 2-ethyl-1-hexanoate, tin(II) ethylcaproate, tin(II) laurate, tin(II)palmitate, dibutyltin(IV) oxide, dibutyltin(IV) dichloride, dibutyltin(IV) diacetate, dibutyltin(IV) dimaleate, dibutyltin(IV) dilaurate, dioctyltin(IV) diacetate, molybdenum glycolate). When catalysts are employed they are preferably employed in a concentration in the range from 0.001 to 2 wt %, by preference in the range from 0.005 to 0.5 wt %, based on the total weight of the reactants.

The present invention further provides compositions comprising at least one adduct according to the invention. The compositions according to the invention are preferably coating compositions. The term coating compositions is in particular to be understood as meaning coating compounds, for example paint compositions, adhesive compositions and sealing compounds.

The compositions according to the invention may comprise further constituents in addition to the compositions according to the invention. The proportion of adduct is thus preferably 15-99 wt %, preferably 25-95 wt % and very particularly preferably 55-95 wt % in each case, based on the total mass of all composition constituents present.

Thus to enhance the flame retardant activity the compositions according to the invention may further comprise flame retardants not reactive with the other composition constituents, i.e. additive flame retardants. When such additive flame retardants are present they are preferably present in proportions of 0.01-85 wt %, preferably 0.01-45 wt %, based on the total mass of all composition constituents present.

Preference is given to non-incorporable organophosphorus flame retardants. Examples of non-incorporable organophosphorus flame retardants include ethylenediamine polyphosphate and phosphoric and phosphonic acid esters, for example triphenyl phosphate, tricresyl phosphate, alkyl phenyl phosphates, diphenyl cresyl phosphate.

Preferred non-incorporable organophosphorus flame retardants are hydrocarbyl(dihydrocarbyl phosphates) of general formula

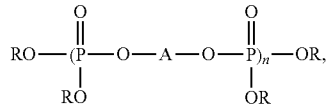

wherein R is preferably an aryl group (for example phenyl, cresyl), A is a connecting group such as arylene (for example phenylene), biarylene (for example biphenyl), two arylene groups connected by a further group such as —CH$_2$—, —C(CH$_3$)$_2$—, —SO$_2$— or —CO—, or alkylene (for example neopentyl) and n is between 1 and 10. Such compounds may be prepared on a large industrial scale from phosphoric acid or phosphoroxy trichloride and diphenols such as resorcinol or bisphenol A (which then form the group A) and monophenols such as phenol and cresol (which then form the group R). Preference is given to 1,3-phenylene tetraphenyl phosphate and oligomers of 1,3-phenylene tetraphenyl phosphate and also to bisphenol A bis(diphenyl phosphate) and oligomers thereof. Preference is also given to derivatives of phosphoric or phosphonic acid which release neither phenol nor cresol upon hydrolysis, examples thereof including trixylyl phosphate, butylated phenyl phosphates and 1,3-phenylene tetraxylenyl phosphate.

Particularly in the case of coating compositions the composition according to the invention may comprise paint-typical components L in addition to the adducts according to the invention.

These paint-typical components L in the compositions according to the invention are preferably present in proportions of 0.1-99 wt %, preferably 5-97 wt % and particularly preferably 10-60 wt % based on the total mass of the composition.

The term paint-typical components L is to be understood as meaning all constituents of a paint described in the literature such as its binders and additives (for example catalysts, stabilizers, photoinitiators, light stabilizers, fillers, pigments, flow control agents or rheology modifiers, for example. sag control agents, microgels or fumed silica, solvents etc., see *Lehrbuch der Lacktechnologie*, T. Brock, M Groteklas, P. Mischke, Vincentz Verlag 2000, Hannover).

The compositions according to the invention preferably comprise at least one catalyst in proportions of 0.01-4 wt % based on the total mass of the composition.

Catalysts are employed to achieve a sufficient curing rate. Preferred catalysts are, in particular, Lewis acids, chelates, salts or particles of transition or other metals, based on titanium, aluminum, tin or zirconium complexes for example, sulphonic acids in free or else neutralized or adducted form as are described in DE 2356768 for example, phosphoric acid or phosphorous acids and derivatives thereof (WO 2008/074491 A1, page 18, lines 1-17), high-boiling acids, guanidines (for example tetramethylguanidine), amidines (for example DBU), quaternary ammonium carboxylates, or else combinations of the cited compounds.

Preference is given to using chelates or salts of transition metals, or high-boiling acids, quaternary ammonium carboxylates, or combinations of the cited compounds.

The catalyst is particularly preferably selected from the group of organic carboxylic acids having a melting point above 60° C. and/or from the group of tetraalkylammonium carboxylates.

Suitable organic carboxylic acids having a melting point above 60° C. (at atmospheric pressure) are compounds which are not volatile at room temperature. Examples of carboxylic acids to be used for advantage include salicylic acid, benzoic acid, citric acid, isophthalic acid, phthalic acid, terephthalic acid and/or trimellitic acid. In the context of the present invention preference is given to using salicylic acid and benzoic acid.

Examples of catalysts from the group of tetraalkylammonium carboxylates include tetramethylammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and/or tetrabutylammonium benzoate. The cited tetraalkylanamonium carboxylates may be added alone or in mixtures. Preference is given to using tetraethylammonium benzoate and/or tetrabutylammonium benzoate.

The catalyst in the composition according to the invention may be composed solely of the abovementioned preferred alternatives carboxylic acid or tetraalkylammonium carboxylate but it is also possible to employ any desired mixtures of the catalysts carboxylic acid or tetraalkylammonium carboxylate. Such mixtures have a ratio of, in particular, 9:1 to 1:9 (m/m). The proportion of carboxylic acid and/or tetraalkylammonium carboxylate is preferably up to 4 wt % based on the total mass of all composition constituents, preferably 0.1 to 4 wt %.

The catalyst employed in the compositions according to the invention may be not only the abovementioned carboxylic acids and/or tetraalkylammonium carboxylates but also, preferably, tin-containing compounds, preferably organotin compounds. Said catalyst is particularly preferably at least one organic tin compound of the formula $R^1_{4-a}SnX_a$, wherein a is 1, 2 or 3, $R^1$ is independently selected from the group consisting of linear or branched, optionally substituted $C_1$-$C_{30}$ alkyl groups, $C_5$-$C_{14}$ cycloalkyl groups or $C_6$-$C_{14}$ aryl groups, triorganylsilyl and also $C_1$-$C_{30}$ diorganylalkoxysilyl groups and X is selected from the group consisting of halogen, —$OR^2$, —$OC(O)R^3$, —OH, —$SR^4$, —$NR^5_2$, —$NHR^6$, —$OSiR^7_3$, —$OSi(OR^8)_3$ where the substituents $R^2$ to $R^8$ are in each case independently of one another selected from optionally substituted $C_1$-$C_8$ alkyl, $C_6$-$C_{14}$ aryl and/or $C_2$-$C_{30}$ alkenyl groups.

The linear or branched, optionally substituted $C_1$-$C_{30}$ alkyl groups cited in the definition of the abovementioned organic tin compounds include those having 1 to 30 carbon atoms, for example, methyl, ethyl, chloroethyl, n-propyl, isopropyl, n-butyl, isobutyl, pentyl, hexyl, heptyl, ethylhexyl, octyl, decyl, undecyl, dodecyl, tridecyl, etc. Preference is then given to butyl, hexyl or octyl.

The $C_5$-$C_{14}$ cycloalkyl groups cited in the definition of the abovementioned organic tin compounds include mono- or polycyclic alkyl groups, such as, for example, cyclopentyl, cyclohexyl, cyclohexylethyl, cyclooctyl, decalinyl, hydrindanyl, bicyclo[2.2.1]heptanyl, bicyclo[2.2.2]octanyl, bicyclo[4.2.3]nonyl.

$C_6$-$C_{14}$ aryl groups include, for example, phenyl, naphthenyl or fluorenyl groups.

Preferred examples of tin-containing compounds suitable as catalysts include alkyltin chlorides, preferably di-n-butyltin dichloride and di-n-octyltin dichloride, alkyltin oxides, preferably di-n-butyltin oxide and di-n-octyltin oxide, dibutyltin carboxylates, preferably di-n-butyltin diacetate, di-n-butyltin dilaurate, di-n-butyltin maleate, bis(2-ethylhexanoate) and di-n-butyltin dineodecanoate, dioctyltin carboxylates, preferably di-n-octyltin diacetate, di-n-octyltin dilaurate, di-n-octyltin maleate, di-n-octyltin bis-2-ethylhexatioate and di-n-octyltin dineodecanoate, and also dialkyltin complexes, preferably di-n-butyltin diacetylacetonate.

The mixtures according to the invention may furthermore particularly preferably employ tin ketonates since these have the advantage of readily dissolving (immediately or after gentle heating) in the compositions according to the invention.

The amount of the tin-containing catalysts in the composition according to the invention is preferably 0.01 to 1.0 wt % and particularly preferably 0.1 to 1 wt % based in each case on the total mass of all composition constituents.

Further examples of preferably employable catalysts for the compositions according to the invention are the catalysts suitable for the production of the adducts according to the invention.

The compositions according to the invention may preferably comprise cobinders as father paint-typical components. Suitable cobinders are in principle any types of binders known to those skilled in the art including, for example, thermoplastic, i.e. noncrosslinkable, binders typically having an average molecular weight of >10 000 g/mol. However, preference is given to using binders comprising reactive functional groups having acidic hydrogen atoms. Suitable binders of the cited type have for example at least one, but preferably two or more, hydroxyl group(s).

When cobinders are present the composition preferably comprises them in proportions of 0.1-30 wt % based on the total mass of the composition.

Preferably employable as co-binders comprising functional groups are hydroxyl group-containing polymers, in particular hydroxyl group-containing polyesters, polyethers, poly(meth)acrylates, polycarbonates and polyurethanes having an OH number of 20 to 500 mg KOH/g and an average molar mass of 250 to 6000 g/mol. In the context of the present invention particular preference is given to using hydroxyl group-containing polyesters or poly(meth)acrylates having an OH number of 20 to 150 mg KOH/g and an average molecular weight of 500 to 6000 g/mol as binder components. The term poly(meth)acrylates is to be understood as meaning both polyacrylates and to polymethacrylates. The hydroxyl number (OHN) is determined in accordance with DIN 53240-2. This method comprises reacting the sample with acetic anhydride in the presence of 4-dimethylaminopyridine as catalyst to acetylate the hydroxyl groups. This affords one molecule of acetic acid per hydroxyl group while the subsequent hydrolysis of the excess acetic anhydride yields two molecules of acetic acid. The consumption of acetic acid is determined by titrimetry from the difference between the main value and a blank value to be carried out in parallel. The molecular weight is determined by means of gel permeation chromatography (GPC). The samples were characterized in tetrahydrofuran eluent in accordance with DIN 55672-1.

Employable as hydroxyl group-containing (meth)acrylic copolymers are resins having a monomer composition as are described, for example, in WO 93/15849 A1 (page 8, line 25 to page 10, line 5), or else in DE 195 29124. The acid number of the (meth)acrylic copolymer to be established by employing a proportion of (meth)acrylic acid as monomer should be 0-30, preferably 3-1.5 mg KOH/g. The number-average molar weight (determined by gel permeation chromatography against a polystyrene standard) of the (meth)acrylic copolymer is preferably 2000-20 000 g/mol and the glass transition temperature is preferably −40° C. to +60° C. The hydroxyl content of the (meth)acrylic copolymers for employment in accordance with the invention, which is to be established by employing a proportion of hydroxyalkyl (meth)acrylates, is preferably 70-250 mg KOH/g and particularly preferably 90-190 mg KOH/g.

Polyester polyols suitable in accordance with the invention are resins having a monomer composition comprising di- and polycarboxylic acids and di- and polyols as are described in, for example, Stoye/Freitag, Lackharze, C. Hamer Verlag, 1996, page 49 or else in WO 93/15849. Also employable as polyester polyols are polyaddition products of caprolactone onto low molecular weight di- and triols as are available under the trade name CAPA (Perstorp) for example. The arithmetically determined number-average molar weight is preferably 500-5000 g/mol, more preferably 800-3000 g/mol and the average functionality is preferably 2.0-4.0, more preferably 2.0-3.5.

Also used in principle as polyols for employment in accordance with the invention and comprising urethane and ester groups are those described in EP 140 186 A2. Preference is given to using polyols which comprise urethane and ester groups and are prepared using HDI, IPDI, trimethyl-hexamethylene diisocyanate (TMDI) or $H_{12}MDI$. The number-average molar weight is preferably 500-2000 g/mol and the average functionality is in particular in the range from 2.0-3.5.

Alkoxysilane-functional binders too are preferentially suitable as cobinders in the compositions according to the invention. Trialkoxysilane-containing binders are particularly preferred. Such binders may be obtained by copolymerization of acrylate or methacrylate monomers with acryloyl- or methacryloyl-functional alkyl trialkoxysilane derivatives (for example Dynasylan® MEMO from Evonik Industries AG) as are described, for example, in WO 92/11328 A1. An alternative synthesis comprises derivatization of hydroxyl group-containing polyethers, polyesters, polycarbonate diols or polyacrylates with isocyanatoalkyl-trialkoxysilane as is described, for example, in Examples 3 and 4 of WO 2008/131715 A1. The synthesis is preferably carried out with isocyanatopropyltrimethoxysilane or isocyanatopropyltriethoxysilane.

The compositions according to the invention may very particularly preferably comprise trialkoxysilane-functional aminosilanes as cobinders. Such aminosilanes preferably conform to the general formula $A_mSiY_n$ where A represents a substituted or unsubstituted aminoalkyl group, a substituted or unsubstituted diaminodialkyl group or a substituted or unsubstituted triaminotrialkyl group, the groups Y are identical or different, wherein Y represents OH, ONa, OK, OR', OCOR', $OSiR'_3$, Cl, Br, I, alkyl or $NR'_2$, m is 1 or 2 and n is 1, 2 or 3, with the proviso that m+n=4, wherein the group R' are independently hydrogen, linear or branched alkyl, cycloalkyl, alkenyl, cycloalkenyl, alkynyl, cycloalkynyl, aryl or heteroaryl groups, each have 1 to 18 carbon atoms and may each optionally be substituted. It is preferable when in is 1 and n is 3. It is further preferable when Y is selected from OH or OR', particular preference being given to OR'. In this case R' is in particular selected from methyl or ethyl groups, particular preference being given to methyl groups.

Preferred aminosilanes are those selected from the group consisting of 3-aminopropyltrimethoxysilane, 3-aminopropyltriedioxysilane, 2-aminoethyl-3-aminopropyltrimethoxysilane, 3-aminopropyl(diethoxymethoxysilane), 3-aminopropyl(tripropoxysilane), 3-aminopropyl(dipropoxymethoxysilane), 3-aminopropyl(tridodecanoxysilane), 3-aminopropyl(tritetradecanoxysilane), 3-aminopropyl(trihexadecanoxysilane), 3-aminopropyl(trioctadecanoxysilane), 3-aminopropyl(didodecanoxy)tetradecanoxysilane, 3-aminopropyl(dodecanoxy)tetradecanoxy(hexadecanoxy)silane, 3-aminopropyl(dimedioxymethylsilane), 3-aminopropyl(methoxydimethylsilane), 3-aminopropyl(hydroxydimethylsilane), 3-aminopropyl(diethoxymethylsilane), 3-aminopropyl(ethoxydimethylsilane), 3-aminopropyl(dipropoxymethylsilane), 3-aminopropyl(propoxydimethylsilane), 3-aminopropyl(diisopropoxymethylsilane), 3-aminopropyl(isopropoxydimethylsilane), 3-aminopropyl(dibutoxymethylsilane), 3-aminopropyl(butoxydimethylsilane), 3-aminopropyl(diisobutoxymethylsilane), 3-aminopropyl(isobutoxydimethylsilane), 3-aminopropyl(didodecanoxymethylsilane), 3-aminopropyl(dodecanoxydimethylsilane), 3-aminopropyl(ditetradecanoxymethylsilane), 3-aminopropyl(tetradecanoxydimethylsilane), 2-aminoethyl(trimethoxysilane), 2-aminoethyl(triethoxysilane), 2-aminoethyl(diethoxymethoxysilane), 2-aminoethyl(tripropoxysilane), 2-aminoethyl(dipropoxymethoxysilane), 2-aminoethyl(tridodecanoxysilane), 2-aminoethyl(tritetradecanoxysilane), 2-aminoethyl(trihexadecanoxysilane), 2-aminoethyl(trioctadecanoxysilane), 2-aminoethyl(didodecanoxy)tetradecanoxysilane, 2-aminoethyl(dodecanoxy)tetradecanoxy(hexadecanoxy)silane, 2-aminoethyl(dimethoxymethylsilane), 2-aminoethyl(methoxydimethylsilane), 2-aminoethyl(diethoxymethylsilane), 2-aminoethyl(ethoxydimethylsilane), 1-aminoethyl(trimethoxysilane), 1-aminomethyl(triethoxysilane), 1-aminomethyl(diethoxymethoxysilane), 1-aminomethyl(dipropoxymethoxysilane), 1-aminomethyl(tripropoxysilane), 1-aminomethyl(trimethoxysilane), 1-aminomethyl(dimethoxymethylsilane), 1-aminomethyl(methoxydimethylsilane), 1-aminomethyl(diethoxymethylsilane), 1-aminomethyl(ethoxydimethylsilane), 3-aminobutyl(trimethoxysilane), 3-aminobutyl(triethoxysilane), 3-aminobutyl(diethoxymethoxysilane), 3-aminobutyl(tripropoxysilane), 3-aminobutyl(dipropoxymethoxysilane), 3-aminobutyl(dimethoxymethylsilane), 3-aminobutyl(diethoxymethylsilane), 3-aminobutyl(dimethylmethoxysilane), 3-aminobutyl(dimethylethoxysilane), 3-aminobutyl(tridodecanoxysilane), 3-aminobutyl(tritetradecanoxysilane), 3-aminobutyl(trihexadecanoxysilane), 3-aminobutyl(didodecanoxy)tetradecanoxysilane, 3-aminobutyl(dodecanoxy)tetradecanoxy(hexadecanoxy)silane, 3-amino-2-methylpropyl(trimethoxysilane), 3-amino-2-methylpropyl(triethoxysilane), 3-amino-2-methylpropyl(diethoxymethoxysilane), 3-amino-2-methylpropyl(tripropoxysilane), 3-amino-2-methylpropyl(dipropoxymethoxysilane), 3-amino-2-methylpropyl(tridodecanoxysilane), 3-amino-2-methylpropyl(tritetradecanoxysilane), 3-amino-2-methylpropyl(trihexadecanoxysilane), 3-amino-2-methylpropyl(trioctadecanoxysilane), 3-amino-2-methylpropyl(didodecanoxy)tetradecanoxysilane, 3-amino-2-methylpropyl(dodecanoxy)tetradecanoxy(hexadecanoxy)silane, 3-amino-2-methylpropyl(dimethoxymethylsilane), 3-amino-2-methylpropyl(methoxydimethylsilane), 3-mercapto-2-methylpropyl(diethoxymethylsilane), 3-mercapto-2-methylpropyl(ethoxydimethylsilane), 3-mercapto-2-methylpropyl(dipropoxymethylsilane), amino-2-methylpropyl(propoxydimethylsilane), 3-amino-2-methylpropyl(diisopropoxymethylsilane), 3-amino-2-methylpropyl(isopropoxydimethylsilane), 3-amino-2-methylpropyl(dibutoxymethylsilane), 3-amino-2-methylpropyl(butoxydimethylsilane), 3-amino-2-methylpropyl(diisobutoxymethylsilane), 3-amino-2-methylpropyl(isobutoxydimethylsilane), 3-amino-2-methylpropyl(didodecanoxymethylsilane), 3-amino-2-methylpropyl(dodecanoxy-dimethylsilane), 3-amino-2-methylpropyl(ditetradecanoxymethylsilane) or 3-amino-2-methylpropyl (tetradecanoxydimethylsilane), triamino-functional propyltrimethoxysilane, bis(3-trimethoxysilylpropyl)amine, bis(3-triethoxysilylpropyl)amine, N-benzyl-N-(2-aminoethyl)-3-aminopropyltrimethoxysilane hydrochloride, N-benzyl-N-(2-aminoethyl)-3-aminopropyltrimethoxysilane hydroacetate, N-(n-butyl)-3-aminopropyltrimethoxysilane, 3-aminopropylmethyldiethoxysilane, N-vinylbenzyl-N-(2-aminoethyl)-3-aminopropylpolysiloxane and N-(2-aminoethyl)-3-aminopropylmethyldimethoxysilane.

Preferred aminosilanes or aminoalkylsilanes are substituted or unsubstituted aminosilane compounds, in particular 3-aminopropyltrimethoxysilane, 3-aminopropyltriethoxysilane, 3-aminopropylmethyldiethoxysilane, N-(2-aminoethyl-3-aminopropyltrimethoxysilane, 2-aminopropyl-3-aminopropyltrimethoxysilane, 2-aminopropyl-3-aminopropyltriethoxysilane, 2-aminoethyl-2-aminoethyl-3-aminopropyltrimethoxysilane, 2-aminoethyl-2-aminoethyl-3-aminopropyltriethoxysilane and N-(n-butyl)-3-aminopropyltrimethoxysilane.

The aminosilane is particularly preferably selected from the group consisting of 3-aminopropyltrimethoxysilane (DYNASYLAN® AMMO), 3-aminopropyltriethoxysilane (DYNASYLAN® AMEO), 3-aminopropylmethyldiethoxysilane (DYNASYLAN® 1505), N-(n-Butyl)-3-aminopropyltrimethoxysilane (DYNASYLAN® 1189) and N-(2-aminoethyl)-3-aminopropyltrimethoxysilane (DYNASYLAN® DAMO), $(H_3CO)_3Si(CH_2)_3NH(CH_2)_3Si(OCH_3)_3$ (bis-AMMO), $(H_5C_2O)_3Si(CH_2)_3NH(CH_2)_3Si(OC_2H_5)_3$ (bis-AMEO), $(H_3CO)_3Si(CH_2)_3NH(CH_2)_2NH(CH_2)_2NH(CH_2)_3Si(OCH_3)_3$ (bis-DAMO) (all from Evonik Industries AG).

It will be appreciated that it is also possible to employ mixtures of he binders described hereinabove. Preferred binders are aminosilanes, adducts of isocyanatoalkyltrialkoxysilanes with polyols as described in EP2641925, polyesters and polyacrylates comprising hydroxyl groups, alone or in mixtures.

The paints for employment in the use according to the invention may be solvent-free or solvent-containing. The paints for employment in accordance with the invention are preferably solvent-free. The paints for employment are further preferably nonaqueous. In the context of the present invention nonaqueous is to be understood as meaning a water content in the composition of not more than 1.0 wt % and preferably not more than 0.5 wt % based on the proportions of all composition constituents. It is particularly preferable when the paint system employed is free from water (not more than 500 ppm water).

The compositions according to the invention are produced by mixing the components described hereinabove. Mixing may be accomplished in mixers known to those skilled in the art, for example stirred vessels, dissolvers, bead mills, roller mills etc, or else in continuous fashion using static mixers or extruders.

The invention likewise provides for the use of the adducts according to the invention for preparing flame retardant coatings, adhesives and sealing compounds, in particular for all flammable mouldings and substrates.

The invention likewise provides for the use of the adducts according to the invention for coating wood, medium-density fibreboard, paper, plastics, textiles, metals, composites or any of the cited substances which have been coated with another coating compound.

Examples of plastics include plexiglass, polyethylene, polycarbonate, polypropylene, polyester, polyamide, polyurethane, polystyrene, polyethylene terephthalate, polysaccharides, polylactic acid, polyhydroxybutyric acid and mixtures of these plastics. The adducts/compositions according to the invention are very particularly suitable for coating plexiglass. The invention thus likewise provides plexiglass coated with an adduct according to the invention/with a composition according to the invention.

The present invention likewise provides metal-coating compositions, in particular car bodies, cycles and motorcycles, building components and household appliances, comprising the adducts or compositions according to the invention.

Even without further exposition it is believed that a person skilled in the art will be able to make the widest use of the above description. The preferred embodiments and examples are therefore to be understood merely as a descriptive disclosure which is not in any way intended to be limiting. The present invention will now be more particularly described with reference to examples. Alternative embodiments of the present invention are obtainable analogously.

Having generally described this invention, a further understanding can be obtained by reference to certain specific examples which are provided herein for purposes of illustration only, and are not intended to be limiting unless otherwise specified.

EXAMPLES

Unless otherwise stated, the reported per cent quantities in the examples are based on weight.

Example 1

Preparation of the Inventive Flame Retardant Adduct Ia 62.18 g of isocyanatopropyltrimethoxysilane (NCO content: 20.2%), 37.81 g of Exolit OP® 560 (from Clariant, as per structural formula (1) where $R^1=R^2=$oligo(ethylene glycol) and $R^3=CH_3$, OH number: 443 mg KOH/g) and 0.01 g of DBTL (dibutyltin(IV) dilaurate) were weighed into a three-necked flask fitted with a reflux cooler and blanketed with nitrogen. The mixture was heated to 60° C. with stirring and the temperature was held at not more than 60° C. After a reaction time of about 3 h at 60° C., an NCO content of <0.1% was achieved. The resulting flame retardant adduct la was a clear liquid which was colorless at room temperature and had a viscosity (23° C.) of 105 mPas.

Comparative Example

Preparation of the Noninventive Adduct Ib (As Per Marosi et al Polymer Degradation and Stability 106 (2014) 63-73)

59.30 g of isocyanatopropyltriethoxysilane (NCO content: 17.1%), 30.51 g of Exolit OP® 560 (from Clariant, as per structural formula (1) where $R^1=R^2=$oligo(ethylene glycol) and $R^3=CH_3$, OH number: 443 mg KOH/g) and 0.09 g of DBTL (dibutyltin(IV) dilaurate) were weighed into a three-necked flask fitted with a reflux cooler and blanketed with nitrogen. The mixture was heated to 60° C. with stirring and the temperature was held at not more than 60° C. After a reaction time of about 6 h at 60° C., an NCO content of <0.1% was achieved. The resulting adduct Ib was a slightly cloudy liquid which was colorless at room temperature.

Example 2

Preparation of Flame Retardant Compositions

Flame retardant compositions were prepared as per the proportions reported in table 1.

TABLE 1

Composition of the flame retardant compositions

| | Flame retardant composition IIa | comparison IIb* |
|---|---|---|
| Flame retardant adduct Ia | 89.6 wt % | 0 wt % |
| Flame retardant adduct Ib | 0 wt % | 89.6 wt % |
| Tego WET 270 | 0.3 wt % | 0.3 wt % |
| Dynasylan AMMO | 10.0 wt % | 10.0 wt % |
| DBTL | 0.1 wt % | 0.1 wt % |

*noninventive

Flame retardant compositions were prepared by combining the adducts Ia and Ib with an aminosilane (Dynasylan AMMO).

The viscosity of the formulations determined as the efflux time in a DIN 4 cup at 23° C. was about 20 seconds.

Determination of Paint Data and Flame Retardant Properties

To determine the characteristics all paints were applied to phosphatized sheet steel (Chemetall Gardobond 26S/60/OC) and to plexiglass by compressed air-assisted spray application using an HPLV gun, and cured at room temperature.

TABLE 2

Properties of the compositions IIa und IIb as paint on sheet steel

| | Flame retardant composition IIa | Comparison IIb |
|---|---|---|
| Pendulum hardness (König) [s] after 1 day at RT | 41 nontacky | not measurable* tacky |

*test pendulum destroys paint

The results in table 2 show that after storage at room temperature for one day the clearcoat prepared from the flame retardant composition IIa according to the invention was nontacky and had a pendulum hardness [König] of 41 s. By contrast, after room temperature curing, the composition as per comparative example IIb was too tacky to be measured. Thus, unlike for the inventive flame retardant composition IIa, it was not possible to obtain a dry, stackable clearcoat for the composition IIb at low curing temperatures.

The inventive flame retardant composition IIa was further applied to plexiglass and subjected to the small burner test (DIN-EN 13501, building material class D). The small burner test showed that the clearcoat prepared from the inventive flame retardant composition IIa had flame retardant properties and passed the tire test to building material class D.

European patent application EP15162900 filed Apr. 9, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An adduct of at least one isocyanatoalkyltrimethoxysilane with at least one flame retardant reactive with the isocyanatoalkyltrimethoxysilane, wherein the at least one flame retardant is an organophosphorus compound, wherein the organophosphorus compound has the structural formula

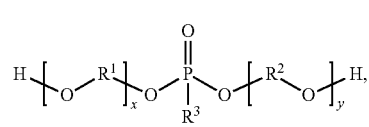

(1)

wherein $R^1$, $R^2$=branched or unbranched alkylene radical having 1 to 24 carbon atoms, substituted or unsubstituted arylene radical having 6 to 20 carbon atoms, substituted or unsubstituted aralkylene radical having 6 to 30 carbon atoms, substituted or unsubstituted alkarylene radical having 6 to 30 carbon atoms, wherein $R^1$ and $R^2$ may be identical or different, $R^3$=H, branched or unbranched alkyl radical having 1 to 24 carbon atoms, substituted or unsubstituted aryl radical having 6 to 20 carbon atoms, substituted or unsubstituted aralkyl radical having 6 to 30 carbon atoms, substituted or unsubstituted alkaryl radical having 6 to 30 carbon atoms, $x$ =1 -50, and $y$ =1 -50.

2. The adduct according to claim 1, wherein the isocyanatoalkyltrimethoxysilane is at least one member selected from the group consisting of isocyanatomethyltrimethoxysilane, 2-isocyanatoethyltrimethoxysilane, 3-isocyanato-n-propyltrimethoxysilane, and 4-isocyanato-n-butyltrimethoxysilane.

3. The adduct according to claim 1, wherein the isocyanatoalkyltrimethoxysilane is 3-isocyanate-n-propyltrimethoxysilane.

4. The adduct according to claim 1, wherein
$R^1$, $R^2$ =branched or unbranched alkylene radical having 1 to 24 carbon atoms.

5. The adduct according to claim 1, wherein the organophosphorus compound has a number-average molecular weight $M_n$ of 60 to 10 000 Daltons.

6. The adduct according to claim 1, wherein a molar ratio between the at least one isocyanatoalkyltrimethoxysilane and the at least one flame retardant is 1:1.

7. A method of preparing an adduct according to claim 1, said method comprising:
reacting the at least one isocyanatoalkyltrimethoxysilane with the at least one flame retardant reactive with the isocyanatoalkyltrimethoxysilane.

8. The method according to claim 7, wherein the at least one isocyanatoalkyltrimethoxysilane is employed with at least one flame retardant reactive with the isocyanatoalkyltrimethoxysilane in a ratio of NCO-reactive radicals of the flame retardant(s) to NCO radicals of the isocyanatoalkyltrimethoxysilane(s) of 0.8:1 to 1.2:1.

9. A composition, comprising:
at least one adduct according to claim 1.

10. The composition according to claim 9, further comprising
at least one catalyst in proportions of 0.01-4 wt % based on a total mass of the composition.

11. The composition according to claim 9, further comprising:

at least one cobinder in proportions of 0.1-30 wt % based on a total mass of the composition.

12. The composition according to claim 11, wherein the cobinder is a trialkoxysilane-functional aminosilane.

13. A flame retardant coating, adhesive or sealing compound, comprising:
   the at least one adduct according to claim 1.

14. A plexiglass, coated with an adduct according to claim 1.

15. An adduct of at least one isocyanatoalkyltrimethoxysilane with at least one flame retardant reactive with the isocyanatoalkyltrimethoxysilane,
   wherein the at least one flame retardant is an organophosphorus compound, and
   wherein the at least one organophosphorus compound is at least one member selected from the group consisting of dimethyl methylphosphonate, diethyl-N,N-bis(2-hydroxyethyl)aminomethyl phosphonate, and dimethylpropane phosphonate.

16. The adduct according to claim 15, wherein the isocyanatoalkyltrimethoxysilane is at least one member selected from the group consisting of isocyanatomethyltrimethoxysilane, 2-isocyanatoethyltrimethoxysilane, 3-isocyanato-n-propyltrimethoxysilane, and 4-isocyanato-n-butyltrimethoxysilane.

17. The adduct according to claim 15, wherein the isocyanoalkyltrimethoxysilane is 3-isocyanato-n-propyltrimethoxysilane.

* * * * *